United States Patent [19]

Lange

[11] Patent Number: 4,471,077

[45] Date of Patent: Sep. 11, 1984

[54] MICROPOROUS POLYLACTIDE POWDERS AND A PROCESS FOR THEIR PREPARATION

[75] Inventor: Wolfgang Lange, Obernburg, Fed. Rep. of Germany

[73] Assignee: Akzo NV, Arnhem, Netherlands

[21] Appl. No.: 496,294

[22] Filed: May 16, 1983

[30] Foreign Application Priority Data

May 14, 1982 [DE] Fed. Rep. of Germany ....... 3218151

[51] Int. Cl.$^3$ .............................................. C08J 9/28
[52] U.S. Cl. ....................................... 521/64; 521/56; 521/60; 521/98; 521/189; 521/921
[58] Field of Search ..................... 521/64, 189, 56, 60, 521/98

[56] References Cited

U.S. PATENT DOCUMENTS

| 4,208,486 | 6/1980 | Patton | 521/64 |
| 4,262,094 | 4/1981 | Johnson | 521/64 |
| 4,391,920 | 7/1983 | Lange | 521/64 |

Primary Examiner—Morton Foelak
Attorney, Agent, or Firm—Michael J. Striker

[57] ABSTRACT

Microporous polylactide powders having an intrinsic isotropic structure being spherical in a shape and containing interconnecting hollow spaces or openings i.e., micropores are obtained by the steps of heating a polylactide in xylene until substantially complete solution is reached; cooling the resultant clear solution; and separating off the xylene.

The microporous powder form powders can have active substances such as a medicament introduced therein i.e. unto the pores and the resultant powder can be used for controllably dispensing the medicament i.e., as a prolonged release form.

8 Claims, No Drawings

MICROPOROUS POLYLACTIDE POWDERS AND A PROCESS FOR THEIR PREPARATION

BACKGROUND OF THE INVENTION

This invention relates to microporous powder from polylactides and to a process for their preparation. More particularly this invention relates to microporous polylactide powders which can have active substances such as medicaments, nutrients, plant growth regulating agents, fragrances and the like introduced therein and the resultant pore filled powders used for controlled dispensing of the active substance.

Processes are already known in which polylactides are dissolved in various solvents possibly in the presence of pore forming agents and the resultant solutions further worked up. The resultant procedures do not, however, provide tricklable microporous powders suitable for having incorporated into the powder particle structure active agents such as aforenoted.

When the polylactide is dissolved in benzene or toluene and the resultant solution cooled, there is obtained on the working up of the solution i.e., removal of the solvent, a solid transparent foil.

There exists therefore a necessity to provide an economically feasible, industrial process for preparing microporous polylactide powders having the improved properties as aforediscussed.

SUMMARY OF THE INVENTION

An object of the invention is to provide a process for preparing microporous, tricklable polylactide powders.

Another object of the invention is to provide a process for preparing microporous, tricklable polylactide powders which are suitable for having incorporated into the powder particles porous structure an active agent such a medicament, nutrient hormone vitamin and the like, a pesticide, a plant growth regulating agent such as a herbicde or defoliant, a trace element(s), a fragrance, etc., for storing and for holding the same and for controllably dispensing or releasing the active agent in its intended locus preferably over a prolonged period of time.

Still another object of the invention is the microporous polylactide powders.

A further object of the invention are the microporous polylactide powders which can be loaded, i.e., charged with solid and/or liquid-form active agents, forming powder form products having active substances distributed in a polymer matrix and specifically within the pores thereof.

These and other objects and advantages of the invention are attained through a process comprising the steps of dissolving a polylactide under warming in xylene cooling the clear solution thereby formed, separating off the xylene and recovering the resultant microporous powder from polylactide.

The dissolution is accomplished by warming to a temperature of from about 50° C. up to the boiling point of the solution in an oil-bath for ½ hour.

The cooling is carried out within 1 hour down to room temperature until the polylactide has separated out of the solution. The solvent is removed for example by suction filtering, any remaining solvent is separated off by drying under vacuum.

As polylactile polymer, there may be used dl-lactic acid, l(+)-lactic acid, d(−)-lactic acid, copolymers of lactic acid and a different hydroxycarboxylic acid as for example glycolic acid. The homopolymers and/or copolymers, can be used singly or in the form of admixtures.

As active agents to be incorporated into the powders, there may be mentioned medicaments including antibiotics, antimicrobial agents, psychotropic agents, antifungal agents, vitamins, nutriments, fragrances, deodorants, trace elements, pesticides, plant growth regulating agents and the like. Incorporation of the active agent is accomplished by treating the unloaded powder with a solution of the active agent in a solvent, filtering off the solvent and evaporating the solvent from the powder by vacuum. The powders are characterized by their microporous nature, the pores interconnect, the tricklable nature of the powders and their suitability for use as a vehicle for providing controlled dispensing and particularly prolonged release of an active substance.

The following examples are given in order to more fully illustrate the invention but are not to be taken as a limitation of the scope thereof.

EXAMPLE 1

90.3 g d(−)-Polylactide having a molecular weight of about 40,000 was dissolved in 400 ml xylene and thereafter without stirring the solution was allowed to cool down to room-temperature for 1 hour. The thusly formed homogeneous mass was separated-off on a suction filter and vacuum dried at 60° C. Hg intrusion measurement of this tricklable powder showed a value equivalent to a 55% pore volume. The particle-size-distribution was <400 μm 4.76%;
400–315 μm 15.75%;
315–200 μm 21.11%;
200–100 μm 51.98%;
100–80 μm 3.81%;
80–0 μm 2.59%.

EXAMPLE 2

The powder form polylactide obtained in accordance with Example 1 is treated with a known defoliant i.e., 2,3-dihydro-5,6-dimethyl-1,4-dithiine-1,1,4,4-tetroxide under conditions whereby the polylactide powder particles take up the defoliant.

The loaded particles can be stored for application to the locus of newly emerging or post-emerging cotton plants for defoliation of the leaves thereof.

I claim:

1. Process for the preparation of microporous polylactide powders which comprises the steps of dissolving a polylactide under warming in xylene; cooling the clear solution thereby formed, separating off the xylene and recovering the resultant microporous polylactide powder.

2. Process according to claim 1, which comprises dissolving the polylactide in the xylene at temperatures of from about 50° C. up to boiling.

3. Process according to claim 1, which comprises separating off the xylene with suction.

4. Process according to claim 1, wherein said polylactide is a homo- or copolymer of dl-lactic acid, l(+)-lactic acid and d(−)-lactic acid.

5. Process according to claim 4, wherein said polylactide is a copolymer of said lactic acid and a different hydroxy carboxylic acid.

6. Process according to claim 5, wherein said copolymer is a copolymer of lactic acid and glycolic acid.

7. Process according to claim 1, wherein said polylactide is d(l)-polylactide.

8. Process according to claim 1, which comprises the additional step of introducing into said microporous polylactide powder an active substance selected from the group consisting of medicinal agents, nutrients, pesticides, plant growth regulating agents, fragrances, deodorants, antibiotics, antimicrobials and antifungals.

* * * * *